US00PP20230P2

(12) United States Plant Patent
Arts

(10) Patent No.: US PP20,230 P2
(45) Date of Patent: Aug. 25, 2009

(54) POINSETTIA PLANT NAMED 'FLOASATUR'

(50) Latin Name: *Euphorbia pulcherrima Willd.*
Varietal Denomination: Floasatur

(75) Inventor: Niels Arts, Aalsmeer (NL)

(73) Assignee: Agriom B.V., De Kwakel (NL)

( * ) Notice: Subject to any disclaimer, the term of this patent is extended or adjusted under 35 U.S.C. 154(b) by 0 days.

(21) Appl. No.: 12/214,240

(22) Filed: Jun. 16, 2008

(51) Int. Cl.
*A01H 5/00* (2006.01)

(52) U.S. Cl. ..... Plt./307

(58) Field of Classification Search ..... Plt./307
See application file for complete search history.

*Primary Examiner*—Kent L Bell
(74) *Attorney, Agent, or Firm*—C. A. Whealy

(57) ABSTRACT

A new and distinct cultivar of Poinsettia plant named 'Floasatur', characterized by its uniform, strong, upright and mounded plant habit; freely branching habit; dark green-colored leaves; early flowering response; large inflorescences with dark red-colored flower bracts; and excellent post-production longevity.

1 Drawing Sheet

Botanical designation: *Euphorbia pulcherrima* Willd.
Cultivar denomination: 'Floasatur'.

BACKGROUND OF THE INVENTION

The present invention relates to a new and distinct cultivar of Poinsettia plant, botanically known as *Euphorbia pulcherrima* Willd., and hereinafter referred to by the name 'Floasatur'.

The new Poinsettia is a product of a planned breeding program conducted by the Inventor in Aalsmeer, The Netherlands. The objective of the breeding program was to develop new low temperature-tolerant Poinsettia cultivars with uniform plant habit and excellent postproduction longevity.

The new Poinsettia originated from a cross-pollination made by the Inventor on Jan. 15, 2005, of a proprietary selection of *Euphorbia pulcherrima* Willd. identified as code number 201108-023, not patented, as the female, or seed, parent with a proprietary selection of *Euphorbia pulcherrima* Willd. identified as code number 200016, not patented, as the male, or pollen, parent. The new Poinsettia was discovered and selected by the Inventor as a flowering plant within the progeny of the stated cross-pollination in a controlled greenhouse environment in Aalsmeer, The Netherlands on Nov. 16, 2005.

Asexual reproduction of the new Poinsettia by terminal vegetative cuttings propagated in a controlled greenhouse environment in Aalsmeer, The Netherlands since July, 2006, has shown that the unique features of this new Poinsettia are stable and reproduced true to type in successive generations of asexual reproduction.

SUMMARY OF THE INVENTION

Plants of the new Poinsettia have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Floasatur'. These characteristics in combination distinguish 'Floasatur' as a new and distinct cultivar of Poinsettia:

1. Uniform, strong, upright and mounded plant habit.
2. Freely branching habit.
3. Dark green-colored leaves.
4. Early flowering response.
5. Large inflorescences with dark red-colored flower bracts.
6. Excellent post-production longevity.

In side-by-side comparisons conducted in Aalsmeer, The Netherlands, plants of the new Poinsettia differed from plants of the female parent selection primarily in flower bract size as plants of the new Poinsettia have larger flower bracts than plants of the female parent selection. In addition, plants of the new Poinsettia have darker red-colored flower bracts than plants of the female parent selection.

In side-by-side comparisons conducted in Aalsmeer, The Netherlands, plants of the new Poinsettia differed from plants of the male parent primarily in flower bract size as plants of the new Poinsettia have larger flower bracts than plants of the male parent selection.

Plants of the new Poinsettia can be compared to plants of *Euphorbia pulcherrima* Willd. 'Fiscor', disclosed in U.S. Plant Pat. No. 9,364. In side-by-side comparisons conducted in Aalsmeer, The Netherlands, plants of the new Poinsettia differed from plants of 'Fiscor' in the following characteristics:

1. Plants of the new Poinsettia had tighter inflorescences than plants of 'Fiscor'.
2. Plants of the new Poinsettia had longer postproduction longevity than plants of 'Fiscor'.
3. Plants of the new Poinsettia had darker red-colored flower bracts than plants of 'Fiscor'.

BRIEF DESCRIPTION OF THE PHOTOGRAPH

The accompanying photograph illustrates the overall appearance of the new Poinsettia. The photograph shows the colors as true as it is reasonably possible to obtain in colored reproductions of this type. Colors in the photograph may differ slightly from the color values cited in the detailed botanical description which accurately describe the colors of the new Poinsettia. The photograph comprises a top perspective view of a typical flowering plant of 'Floasatur'.

DETAILED BOTANICAL DESCRIPTION

Plants used for the aforementioned photograph and following observations and measurements were grown in 13-cm containers in De Kwakel, The Netherlands during the autumn and winter in a glass-covered greenhouse and under conditions and cultural practices which approximate those generally used in commercial Poinsettia production. During the first ten weeks of production of the plants, day and night temperatures averaged 20° C. and during the finishing production phase, day and night temperatures averaged 17° C. Light levels throughout the entire production period were about 200 Watts per square meter. Plants were pinched one time and were forced into flower under short day/long night photoperiodic conditions. Plants were 18 weeks from planting when the photograph and the detailed description were taken. In the following description, color references are made to The Royal Horticultural Society Colour Chart, 1995 Edition, except where general terms of ordinary dictionary significance are used.

Botanical classification: *Euphorbia pulcherrima* Willd. 'Floasatur'.

Parentage:

*Female, or seed, parent.*—Proprietary selection of *Euphorbia pulcherrima* Willd. identified as code number 201108-023, not patented.

*Male, or pollen, parent.*—Proprietary selection of *Euphorbia pulcherrima* Willd. identified as code number 200016, not patented.

Propagation:

*Type.*—Terminal vegetative cuttings.

*Time to initiate roots.*—About 10 to 14 days at 22° C.

*Time to produce a rooted young plant.*—About four weeks at 22° C.

*Root description.*—Fibrous, medium to thick; white in color.

*Rooting habit.*—Freely branching; moderately dense.

Plant description:

*Plant habit and form.*—Uniform, strong, upright and mounded plant habit; inverted triangle. Inflorescences positioned above the foliar plane. Vigorous growth habit.

*Plant height.*—About 25 cm.

*Plant diameter or spread.*—About 40 cm.

*Lateral branch description.*—Quantity: Freely branching habit, about five lateral branches develop after pinching. Length: About 20 cm. Diameter: About 6 mm. Internode length: About 1 cm to 3 cm. Strength: Strong. Texture: Smooth, glabrous. Color: Close to 146A.

*Foliage description.*—Arrangement: Alternate, simple. Length: About 11 cm. Width: About 8 cm. Shape: Ovate. Apex: Acute. Base: Obtuse. Margin: Entire or lobed. Venation pattern: Pinnate. Texture, upper and lower surfaces: Smooth, glabrous. Color: Developing foliage, upper surface: Darker than 144A. Developing foliage, lower surface: Close to 147B. Fully expanded foliage, upper surface: Close to 139A; venation, close to 187B. Fully expanded foliage, lower surface: Close to 189A; venation, close to 147B. Petiole: Length: About 5 cm. Diameter: About 2 mm. Texture, upper and lower surfaces: Smooth, glabrous. Color, upper and lower surfaces: Close to 183B.

Inflorescence description:

*Inflorescence type and habit.*—Inflorescences are compound corymbs of cyathia with colored flower bracts subtending the cyathia. One inflorescence per lateral branch. Flowers are not fragrant. Flowers persistent. Inflorescences positioned above the foliage.

*Natural flowering season.*—Autumn/winter; inflorescence initiation and development is induced under long nyctoperiod conditions. Early flowering response, plants begin flowering about seven weeks after the start of short day/long day photoperiodic treatments.

*Post-production longevity.*—Excellent post-production longevity; plants of the new Poinsettia maintain good substance and bract color for about six weeks under interior conditions and for about eight weeks in the greenhouse.

*Inflorescence size.*—Diameter: About 20 cm. Height (depth): About 5 cm.

*Flower bracts.*—Quantity per inflorescence: About 13. Length, largest bracts: About 10 cm. Width, largest bracts: About 6.5 cm. Shape: Ovate. Apex: Acuminate. Base: Obtuse. Margin: Entire. Texture, upper and lower surfaces: Smooth, glabrous. Venation pattern: Pinnate. Color: Developing or transitional bracts, upper surface: Close to 187B. Developing or transitional bracts, lower surface: Close to 46C. Fully developed bracts, upper surface: Close to 53B. Fully developed bracts, lower surface: Close to 46C. Venation, upper and lower surfaces: Similar to flower bract color. Bract petiole: Length: About 2 cm. Diameter: About 2 mm. Texture, upper and lower surfaces: Smooth, glabrous. Color, upper and lower surfaces: Close to 187B.

*Cyathia.*—Quantity per corymb: About seven. Diameter of cyathia cluster: About 2 cm. Length: About 1 cm. Width: About 5 mm. Shape: Oval. Color, immature: Close to 3A. Color, mature: Close to 14A; towards the apex, close to 53B. Nectaries: Quantity per cyathium: Usually one or two. Size: About 6 mm. Color: Close to 15C.

*Peduncles.*—Length: About 5 mm to 10 mm. Diameter: About 5 mm. Strength: Strong. Aspect: Upright. Texture: Smooth, glabrous. Color: Close to 146A.

*Reproductive organs.*—Stamens: Quantity per cyathium: About eight to ten. Anther shape: Oval. Anther length: About 0.5 mm. Anther color: Close to 6B. Amount of pollen: Abundant. Pollen color: Close to 12A. Pistils: Quantity per cyathium: About three. Pistil length: About 3 mm. Style length: About 3 mm. Style color: Close to 46B. Stigma shape: Rounded to oval. Stigma color: Close to 46B. Ovary color: Close to 143A.

*Seed/fruit.*—Seed and fruit development have not been observed.

Disease/pest resistance: Plants of the new Poinsettia have not been shown to be resistant to pathogens and pests common to Poinsettias.

Temperature tolerance: Plants of the new Poinsettia have been observed to tolerate temperatures ranging from about 17° C. to about 35° C.

It is claimed:

1. A new and distinct Poinsettia plant named 'Floasatur' as illustrated and described.

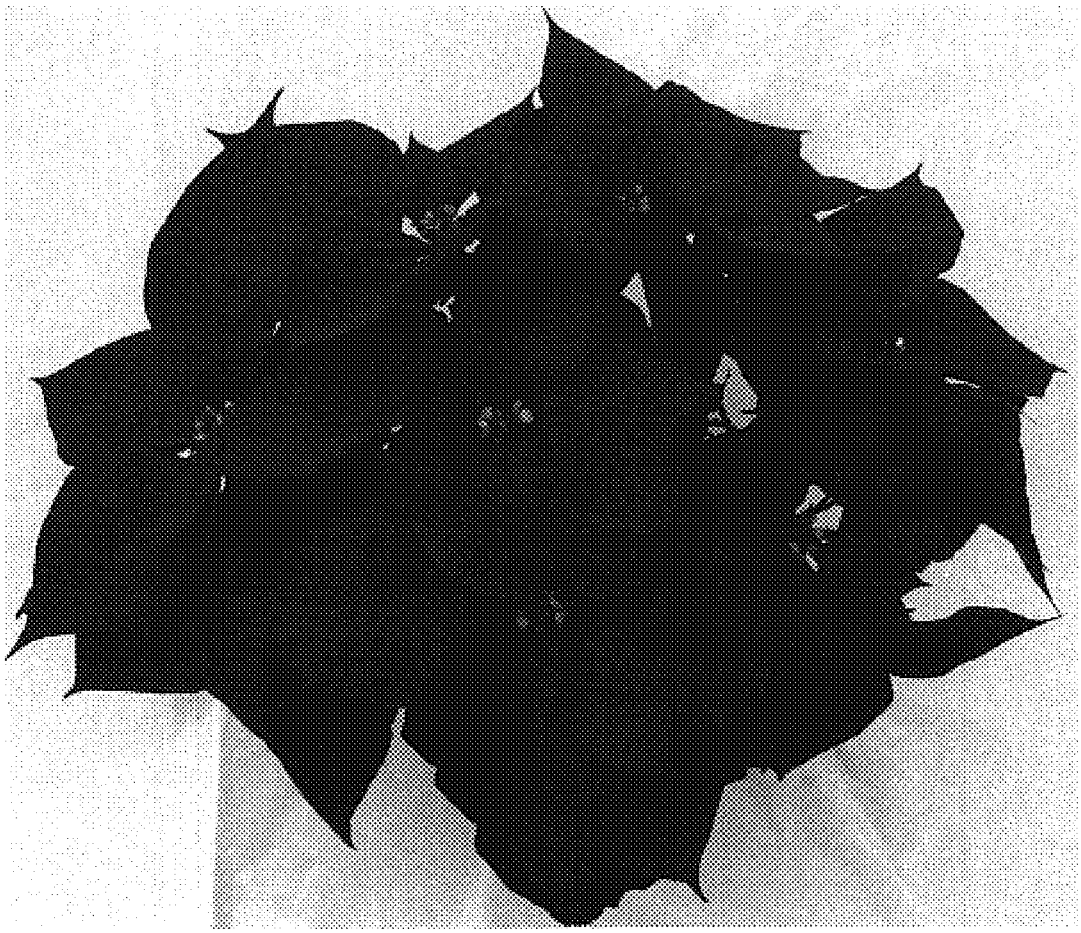

* * * * *